(12) United States Patent  
Huang et al.

(10) Patent No.: US 8,318,716 B2
(45) Date of Patent: Nov. 27, 2012

(54) CARBAPENEM DERIVATIVES

(75) Inventors: Zhenhua Huang, Shandong (CN); Yanyan Dong, Shandong (CN)

(73) Assignee: KBP Biosciences Co., Ltd., Jinan (CN)

( * ) Notice: Subject to any disclaimer, the term of this patent is extended or adjusted under 35 U.S.C. 154(b) by 323 days.

(21) Appl. No.: 12/650,742

(22) Filed: Dec. 31, 2009

(65) Prior Publication Data

US 2011/0160177 A1   Jun. 30, 2011

(51) Int. Cl.
C07D 477/20 (2006.01)
A61P 31/04 (2006.01)
A61K 31/407 (2006.01)

(52) U.S. Cl. ................ 514/210.13; 540/350
(58) Field of Classification Search ............. 540/350; 514/210.13
See application file for complete search history.

(56) References Cited

U.S. PATENT DOCUMENTS

| | | | | |
|---|---|---|---|---|
| 5,541,178 | A * | 7/1996 | Betts et al. | 514/210.13 |
| 5,554,606 | A * | 9/1996 | Betts et al. | 514/210.13 |
| 6,180,622 | B1 | 1/2001 | Aihara et al. | |
| 2010/0197653 | A1* | 8/2010 | Huang et al. | 514/210.13 |

FOREIGN PATENT DOCUMENTS

| | | | |
|---|---|---|---|
| CN | 101333218 A | * | 12/2008 |
| CN | 101372489 A | * | 2/2009 |
| EP | 0126587 A1 | | 11/1984 |
| WO | WO 2006/035300 A2 | | 4/2006 |
| WO | WO 2009000163 A1 | * | 12/2008 |
| WO | WO 2011143935 A1 | * | 11/2011 |
| WO | WO 2011150679 A1 | * | 12/2011 |

OTHER PUBLICATIONS

Lee et al., "Synthesis and Antibacterial Evaluation of 1β-Methyl-2-(5-substituted heterocyclic carbamoyl)pyrrolidin-3-ylthio)carbapenem Derivatives," Arch. Pharm. Pharm. Med. Chem. 337:391-397 (2004).
Sunagawa et al., "A Novel Carbapenem Antibiotic, SM-7338 Structure-Activity Relationships," J. Antiobiotics 43(5):519-532 (1990).

* cited by examiner

Primary Examiner — Mark Berch
(74) Attorney, Agent, or Firm — Cooley LLP

(57) ABSTRACT

The present invention includes novel carbapenem derivatives having structural formula (I) or (II):

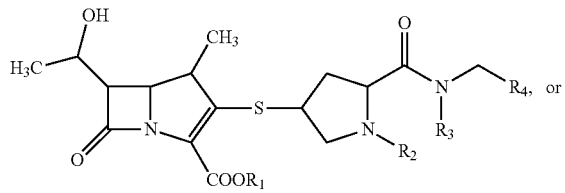

(I)

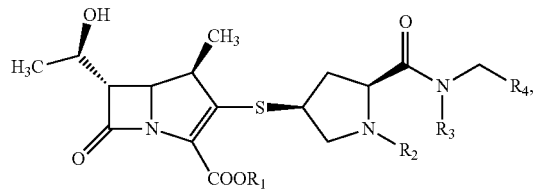

(II)

wherein $R^1$, $R^2$, $R^3$, $R^4$ are described in the specification. The present invention also provides pharmaceutical compositions comprising the novel carbapenem derivatives and the use of the novel carbapenem derivatives for treating infectious diseases.

10 Claims, No Drawings

CARBAPENEM DERIVATIVES

FIELD OF THE INVENTION

The present invention generally relates to the pharmaceutical field, and specifically relates to novel carbapenem derivatives and their therapeutic use.

BACKGROUND OF THE INVENTION

Carbapenem antibiotics are a type of β-lactam antibiotics initially developed in 1970s. Carbapenems attracted a lot of attention for the broad antibacterial spectrum, potent antibacterial activity and stability towards β-lactamase. The structural features of carbapenems include: (1) the sulfur atom at 1-position of the parent core of penam is replaced by a carbon atom, a feature that activates the β-lactam antibiotics by ring strain introduced by the fused five-membered ring; (2) a double bond is introduced at 2-position, which activates the antibiotics by the delocalization of the β-lactam nitrogen lone pair into a conjugated double bond system; and (3) a hydroxyethyl group side chain at 6-position is trans-configuration.

There are a number of carbapenem type of antibiotics available on the market, such as imipenem, meropenem, ertapenem, doripenem, panipenem, and bioapenem. Those carbapenem antibiotics have certain clinical shortcomings including relatively short half life and intravenous administration. Furthermore, the microbes have grown to be more drug resistance due to the overuse of antibiotics. Thus, there is a strong need to develop novel carbapenem antibiotics.

SUMMARY OF THE INVENTION

In one embodiment, the present invention provides a compound of formula (I):

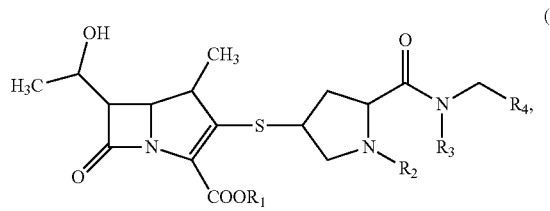

or a pharmaceutically acceptable salt, solvate, ester, and/or prodrug thereof; wherein $R^1$ is hydrogen or a carboxyl protecting group; $R^2$ is hydrogen or an amino-protecting group; $R^3$ is hydrogen or lower alkyl; and $R^4$ is phenyl or substituted phenyl; wherein the substituted phenyl comprises one or more substituents selected from the group consisting of halogen; hydroxyl; carboxyl; amino; nitro; cyano; lower alkyl; substituted lower alkyl; lower alkoxy; substituted lower alkoxy; aminosulfonyl; lower alkylaminosulfonyl; and a combination thereof; wherein the substituted lower alkyl and the substituted lower alkoxy each independently comprise one or more substituents selected from the group consisting of halogen; hydroxyl; carboxyl; amino; nitro; cyano; and a combination thereof.

In another embodiment, the present invention provides a compound of formula (I):

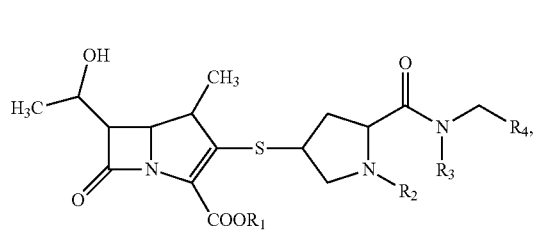

or a pharmaceutically acceptable salt, solvate, ester, and/or prodrug thereof;
wherein $R^1$ is a hydrogen atom or a carboxyl protecting group; $R^2$ is a hydrogen atom or an amino-protecting group; $R^3$ is a hydrogen atom or a lower alkyl; and $R^4$ is a phenyl or substituted phenyl; wherein the substituted phenyl comprises one or more substituents selected from the group consisting of sulfo; carbamoyl; lower alkyl; substituted lower alkyl; lower alkoxy; substituted lower alkoxy; lower alkylcarbonyl; substituted lower alkylcarbonyl; lower alkylcarbonyloxy; substituted lower alkylcarbonyloxy; lower alkylsulphonyl; substituted lower alkylsulphonyl; lower alkylamido; substituted lower alkylamido; lower alkylcarbamoyl; substituted lower alkylcarbamoyl; lower alkylsulphonamido; substituted lower alkylsulphonamido; and a combination thereof; wherein the substituted lower alkyl and the substituted lower alkoxy each independently comprise one or more substituents selected from the group consisting of sulfo; aminosulphonyl; carbamoyl; and a combination thereof; wherein the substituted lower alkylcarbonyl; the substituted lower alkylcarbonyloxy; the substituted lower alkylsulphonyl; the substituted lower alkylamido; the substituted lower alkylcarbamoyl; and the substituted lower alkylsulphonamido each independently comprise one or more substituents selected from the group consisting of halogen; hydroxyl; carboxyl; amino; nitro; cyano; sulfo; aminosulfonyl; carbamoyl; and a combination thereof.

In another embodiment, the present invention provides a compound of formula (II):

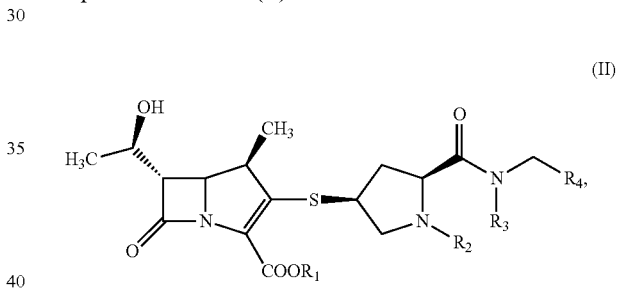

or a pharmaceutically acceptable salt, solvate, ester, and/or prodrug thereof;
wherein $R^1$ is a hydrogen atom or a carboxyl protecting group; $R^2$ is a hydrogen atom or an amino-protecting group; $R^3$ is a hydrogen atom or a lower alkyl; and $R^4$ is a phenyl or substituted phenyl; wherein the substituted phenyl comprises one or more substituents selected from the group consisting of sulfo; carbamoyl; lower alkyl; substituted lower alkyl; lower alkoxy; substituted lower alkoxy; lower alkylcarbonyl; substituted lower alkylcarbonyl; lower alkylcarbonyloxy; substituted lower alkylcarbonyloxy; lower alkylsulphonyl; substituted lower alkylsulphonyl; lower alkylamido; substituted lower alkylamido; lower alkylcarbamoyl; substituted lower alkylcarbamoyl; lower alkylsulphonamido; substituted lower alkylsulphonamido; and a combination thereof; wherein the substituted lower alkyl and the substituted lower alkoxy each independently comprise one or more substituents selected from the group consisting of sulfo; aminosulphonyl; carbamoyl; and a combination thereof; wherein the substituted lower alkylcarbonyl; the substituted lower alkylcarbonyloxy; the substituted lower alkylsulphonyl; the substituted lower alkylamido; the substituted lower alkylcarbamoyl; and the substituted lower alkylsulphonamido each independently comprise one or more substituents selected from the group consisting of halogen; hydroxyl; carboxyl; amino; nitro; cyano; sulfo; aminosulfonyl; carbamoyl; and a combination thereof.

In yet another embodiment, the present invention provides a pharmaceutical composition comprising a compound of the present invention, or a pharmaceutically acceptable salt, solvate, ester, and/or prodrug thereof; and one or more pharmaceutically acceptable carriers.

In yet another embodiment, the present invention provides a method of treating an infectious disease in a patient in need thereof comprising administering to the patient a therapeutically effective amount of a compound of the present invention, or a pharmaceutically acceptable salt, solvate, ester, and/or prodrug thereof.

DETAILED DESCRIPTION OF THE INVENTION

The present invention provides novel carbapenem derivatives exhibiting potent antibacterial activity, broad antibacterial spectrum, excellent stability to renal dehydropeptidase-I (DHP-I), and long half life. The present compounds can be used to treat various microbial infections, and are capable of treating hospital-based infections.

Compounds:

In one embodiment, the present invention provides a compound of formula (I):

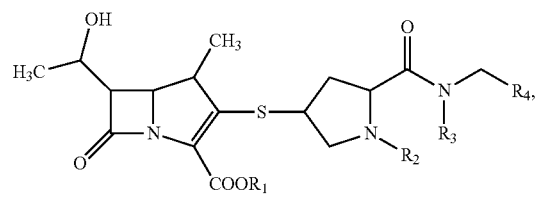

(I)

or a pharmaceutically acceptable salt, solvate, ester, and/or prodrug thereof;
wherein $R^1$ is hydrogen or a carboxyl protecting group; $R^2$ is hydrogen or an amino-protecting group; $R^3$ is hydrogen or lower alkyl; and $R^4$ is phenyl or substituted phenyl. In one embodiment, the substituted phenyl comprises one or more substituents selected from the group consisting of halogen; hydroxyl; carboxyl; amino; nitro; cyano; lower alkyl; substituted lower alkyl; lower alkoxy; substituted lower alkoxy; aminosulfonyl; lower alkylaminosulfonyl; and a combination thereof; wherein the substituted lower alkyl and the substituted lower alkoxy each independently comprise one or more substituents selected from the group consisting of halogen; hydroxyl; carboxyl; amino; nitro; cyano; and a combination thereof. In another embodiment, the substituted phenyl is a mono-substituted phenyl. In one embodiment of formula (I), $R^3$ is hydrogen, methyl, ethyl, or propyl; $R^4$ is a phenyl or substituted phenyl; wherein the substituted phenyl comprises one or more substituents selected from the group consisting of halogen; hydroxyl; carboxyl; amino; lower alkyl; substituted lower alkyl; lower alkoxy; substituted lower alkoxy; aminosulfonyl; and a combination thereof; and wherein the substituted lower alkyl and the substituted lower alkoxy each independently comprise one or more substituents selected from the group consisting of halogen; hydroxyl; carboxyl; amino; and a combination thereof. In another embodiment of formula (I), $R^1$ represents hydrogen atom; $R^2$ represents hydrogen atom; $R^3$ represents hydrogen atom or methyl; and $R^4$ is a phenyl or substituted phenyl; wherein the substituted phenyl comprises one or more substituents selected from the group consisting of methyl; ethyl; carboxyl; carboxymethyl; carboxyethyl; methoxy; trifluoromethoxy; aminosulfonyl; and a combination thereof. In one embodiment of formula (I), the compound has the following structural formula:

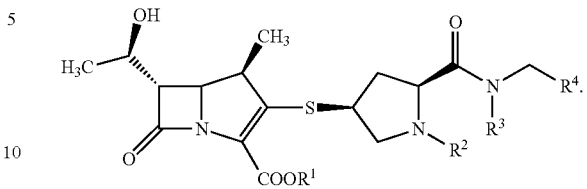

In another embodiment, the present invention provides a compound of formula (I):

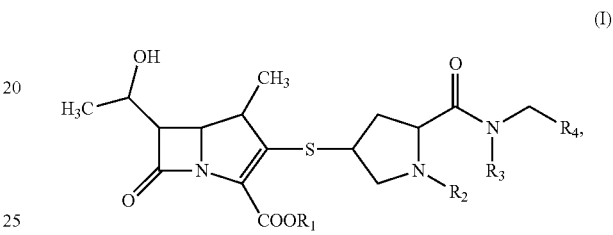

(I)

or a pharmaceutically acceptable salt, solvate, ester, and/or prodrug thereof;
wherein $R^1$ is a hydrogen atom or a carboxyl protecting group; $R^2$ is a hydrogen atom or an amino-protecting group; $R^3$ is a hydrogen atom or a lower alkyl; and $R^4$ is a phenyl or substituted phenyl. In one embodiment, the substituted phenyl comprises one or more substituents selected from the group consisting of sulfo; carbamoyl; lower alkyl; substituted lower alkyl; lower alkoxy; substituted lower alkoxy; lower alkylcarbonyl; substituted lower alkylcarbonyl; lower alkylcarbonyloxy; substituted lower alkylcarbonyloxy; lower alkylsulphonyl; substituted lower alkylsulphonyl; lower alkylamido; substituted lower alkylamido; lower alkylcarbamoyl; substituted lower alkylcarbamoyl; lower alkylsulphonamido; substituted lower alkylsulphonamido; and a combination thereof; wherein the substituted lower alkyl and the substituted lower alkoxy each independently comprise one or more substituents selected from the group consisting of sulfo; aminosulphonyl; carbamoyl; and a combination thereof; wherein the substituted lower alkylcarbonyl; the substituted lower alkylcarbonyloxy; the substituted lower alkylsulphonyl; the substituted lower alkylamido; the substituted lower alkylcarbamoyl; and the substituted lower alkylsulphonamido each independently comprise one or more substituents selected from the group consisting of halogen; hydroxyl; carboxyl; amino; nitro; cyano; sulfo; aminosulfonyl; carbamoyl; and a combination thereof. In another embodiment, the substituted phenyl is a mono-substituted phenyl. In one embodiment of formula (I), $R^3$ is hydrogen, methyl, ethyl, or propyl; $R^4$ is a phenyl or substituted phenyl; wherein the substituted phenyl comprises one or more substituents selected from the group consisting of halogen; hydroxyl; carboxyl; amino; lower alkyl; substituted lower alkyl; lower alkoxy; substituted lower alkoxy; aminosulfonyl; and a combination thereof; and wherein the substituted lower alkyl and the substituted lower alkoxy each independently comprise one or more substituents selected from the group consisting of halogen; hydroxyl; carboxyl; amino; and a combination thereof. In another embodiment of formula (I), $R^1$ represents hydrogen atom; $R^2$ represents hydrogen atom; $R^3$ represents hydrogen atom or methyl; and $R^4$ is a phenyl or substituted phenyl; wherein the substituted phenyl comprises one or more substituents selected from the group consisting of methyl; ethyl; carboxyl; carboxymethyl; carboxyethyl; methoxy; trifluoromethoxy; aminosulfonyl; and a combination thereof. In one embodiment of formula (I), the compound has the following structural formula:

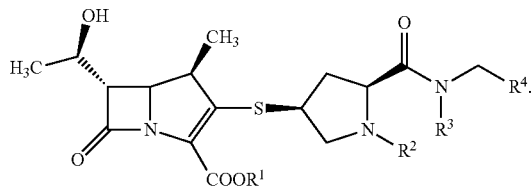

In another embodiment, the present invention provides a compound of formula (II):

(II)

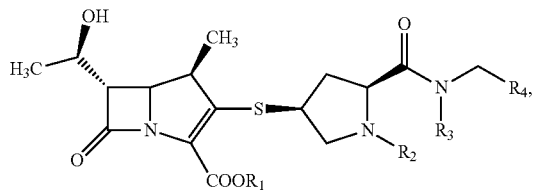

or a pharmaceutically acceptable salt, solvate, ester, and/or prodrug thereof;
wherein $R^1$ is a hydrogen atom or a carboxyl protecting group; $R^2$ is a hydrogen atom or an amino-protecting group; $R^3$ is a hydrogen atom or a lower alkyl; and $R^4$ is a phenyl or substituted phenyl. In one embodiment, the substituted phenyl comprises one or more substituents selected from the group consisting of sulfo; carbamoyl; lower alkyl; substituted lower alkyl; lower alkoxy; substituted lower alkoxy; lower alkylcarbonyl; substituted lower alkylcarbonyl; lower alkylcarbonyloxy; substituted lower alkylcarbonyloxy; lower alkylsulphonyl; substituted lower alkylsulphonyl; lower alkylamido; substituted lower alkylamido; lower alkylcarbamoyl; substituted lower alkylcarbamoyl; lower alkylsulphonamido; substituted lower alkylsulphonamido; and a combination thereof; wherein the substituted lower alkyl and the substituted lower alkoxy each independently comprise one or more substituents selected from the group consisting of sulfo; aminosulphonyl; carbamoyl; and a combination thereof; wherein the substituted lower alkylcarbonyl; the substituted lower alkylcarbonyloxy; the substituted lower alkylsulphonyl; the substituted lower alkylamido; the substituted lower alkylcarbamoyl; and the substituted lower alkylsulphonamido each independently comprise one or more substituents selected from the group consisting of halogen; hydroxyl; carboxyl; amino; nitro; cyano; sulfo; aminosulfonyl; carbamoyl; and a combination thereof. In another embodiment, the substituted phenyl is a mono-substituted phenyl. In one embodiment of formula (II), $R^3$ is hydrogen, methyl, ethyl, or propyl; $R^4$ is a phenyl or substituted phenyl; wherein the substituted phenyl comprises one or more substituents selected from the group consisting of halogen; hydroxyl; carboxyl; amino; lower alkyl; substituted lower alkyl; lower alkoxy; substituted lower alkoxy; aminosulfonyl; and a combination thereof; and wherein the substituted lower alkyl and the substituted lower alkoxy each independently comprise one or more substituents selected from the group consisting of halogen; hydroxyl; carboxyl; amino; and a combination thereof. In another embodiment of formula (II), $R^1$ represents hydrogen atom; $R^2$ represents hydrogen atom; $R^3$ represents hydrogen atom or methyl; and $R^4$ is a phenyl or substituted phenyl; wherein the substituted phenyl comprises one or more substituents selected from the group consisting of methyl; ethyl; carboxyl; carboxymethyl; carboxyethyl; methoxy; trifluoromethoxy; aminosulfonyl; and a combination thereof. In one embodiment of formula (I), the compound has the following structural formula:

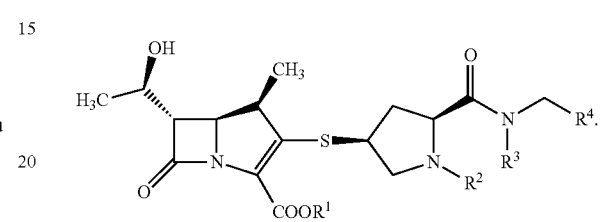

In some specific embodiments, the present invention provides compounds selected from the group consisting of

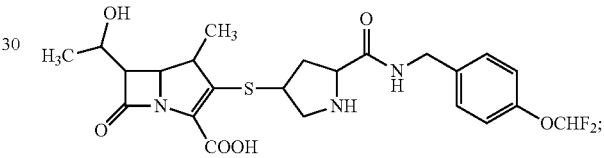

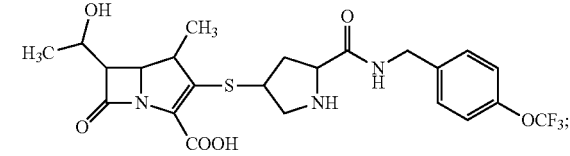

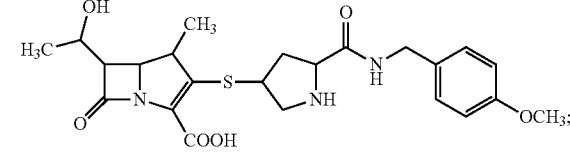

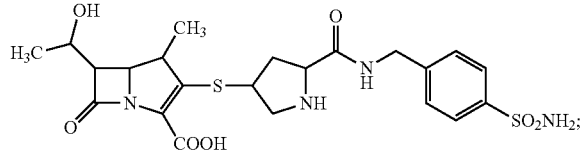

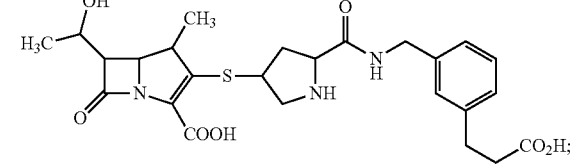

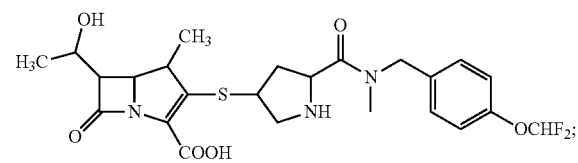

-continued

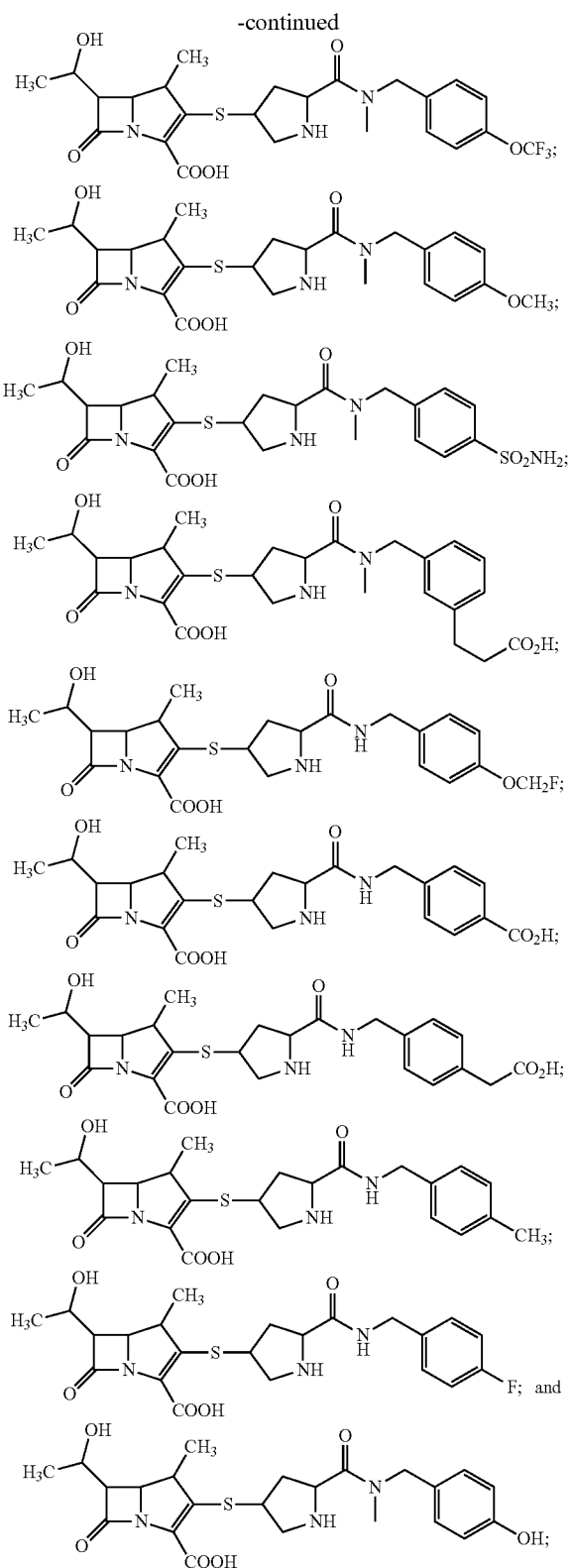

or a pharmaceutically acceptable salt, solvate, ester, and/or prodrug thereof.

In some specific embodiments, the present invention provides compounds selected from the group consisting of
(4R,5S,6S)-3-((3S,5S)-5-(4-(difluoromethoxy)benzylcarbamoyl)pyrrolidin-3-ylthio)-6-((R)-1-hydroxyethyl)-4-methyl-7-oxo-1-azabicyclo[3.2.0]hept-2-ene-2-carboxylic acid;
(4R,5S,6S)-6-((R)-1-hydroxyethyl)-4-methyl-7-oxo-3-((3S,5S)-5-(4-(trifluoromethoxy)benzylcarbamoyl)pyrrolidin-3-ylthio)-1-azabicyclo[3.2.0]hept-2-ene-2-carboxylic acid;
(4R,5S,6S)-6-((R)-1-hydroxyethyl)-3-(3S,5S)-5-(4-methoxybenzylcarbamoyl)pyrrolidin-3-ylthio)-4-methyl-7-oxo-1-azabicyclo[3.2.0]hept-2-ene-2-carboxylic acid;
(4R,5S,6S)-6-((R)-1-hydroxyethyl)-4-methyl-7-oxo-3-((3S,5S)-5-(4-sulfamoylbenzylcarbamoyl)pyrrolidin-3-ylthio)-1-azabicyclo[3.2.0]hept-2-ene-2-carboxylic acid;
(4R,5S,6S)-3-((3S,5S)-5-(3-(2-carboxyethyl)benzylcarbamoyl)pyrrolidin-3-ylthio)-6-((R)-1-hydroxyethyl)-4-methyl-7-oxo-1-azabicyclo[3.2.0]hept-2-ene-2-carboxylic acid;
(4R,5S,6S)-3-((3S,5S)-5-(4-(difluoromethoxy)benzyl)(methyl)carbamoyl)pyrrolidin-3-ylthio)-6-((R)-1-hydroxyethyl)-4-methyl-7-oxo-1-azabicyclo[3.2.0]hept-2-ene-2-carboxylic acid;
(4R,5S,6S)-6-((R)-1-hydroxyethyl)-4-methyl-3-((3S,5S)-5-(methyl(4-(trifluoromethoxy)benzyl)carbamoyl)pyrrolidin-3-ylthio)-7-oxo-1-azabicyclo[3.2.0]hept-2-ene-2-carboxylic acid;
(4R,5S,6S)-6-((R)-1-hydroxyethyl)-3-((3S,5S)-5-((4-methoxybenzyl)(methyl)carbamoyl)pyrrolidin-3-ylthio)-4-methyl-7-oxo-1-azabicyclo[3.2.0]hept-2-ene-2-carboxylic acid;
(4R,5S,6S)-6-((R)-1-hydroxyethyl)-4-methyl-3-((3S,5S)-5-(methyl(4-sulfamoylbenzyl)carbamoyl)pyrrolidin-3-ylthio)-7-oxo-1-azabicyclo[3.2.0]hept-2-ene-2-carboxylic acid;
(4R,5S,6S)-3-((3S,5S)-5-((3-(2-carboxyethyl)benzyl)(methyl)carbamoyl)pyrrolidin-3-ylthio)-6-((R)-1-hydroxyethyl)-4-methyl-7-oxo-1-azabicyclo[3.2.0]hept-2-ene-2-carboxylic acid;
(4R,5S,6S)-3-((3S,5S)-5-(4-(fluoromethoxy)benzylcarbamoyl)pyrrolidin-3-ylthio)-6-((R)-1-hydroxyethyl)-4-methyl-7-oxo-1-azabicyclo[3.2.0]hept-2-ene-2-carboxylic acid;
(4R,5S,6S)-3-((3S,5S)-5-(4-carboxybenzylcarbamoyl)pyrrolidin-3-ylthio)-6-(R)-1-hydroxyethyl)-4-methyl-7-oxo-1-azabicyclo[3.2.0]hept-2-ene-2-carboxylic acid;
(4R,5S,6S)-3-((3S,5S)-5-(4-(carboxymethyl)benzylcarbamoyl)pyrrolidin-3-ylthio)-6-((R)-1-hydroxyethyl)-4-methyl-7-oxo-1-azabicyclo[3.2.0]hept-2-ene-2-carboxylic acid;
(4R,5S,6S)-6-((R)-1-hydroxyethyl)-4-methyl-3-((3S,5S)-5-(4-methylbenzylcarbamoyl)pyrrolidin-3-ylthio)-7-oxo-1-azabicyclo[3.2.0]hept-2-ene-2-carboxylic acid;
(4R,5S,6S)-3-((3S,5S)-5-(4-fluorobenzylcarbamoyl)pyrrolidin-3-ylthio)-6-(R)-1-hydroxyethyl)-4-methyl-7-oxo-1-azabicyclo[3.2.0]hept-2-ene-2-carboxylic acid; and
(4R,5S,6S)-3-((3S,5S)-5-((4-hydroxybenzyl)(methyl)carbamoyl)pyrrolidin-3-ylthio)-6-((R)-1-hydroxyethyl)-4-methyl-7-oxo-1-azabicyclo[3.2.0]hept-2-ene-2-carboxylic acid;
or a pharmaceutically acceptable salt, solvate, ester, and/or prodrug thereof.

DEFINITIONS

The terms "a", "an", and "the" refer to "one or more" when used in this application, including the claims. Thus, for example, reference to "a carrier" includes mixtures of one or more carriers, two or more carriers, and the like.

The term "present compound(s)", "compound(s) of the present invention", or "novel carbapenem derivative(s)" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein include all of their isomeric forms, i.e., isomers. The term "isomer" refers to all epimeric, diastereomeric and tautomeric forms. When a bond is drawn as a wedge, this indicates that in three dimensions the bond would be coming out of the paper and when a bond is hatched, this indicates that in three dimensions the bond would be going back into the paper. The compounds of the formulae (I) and (II) may contain a number of stereo centers, including those at the position 4, 5 and 6.

The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention.

The term "halogen", as used herein, means fluorine atom, chlorine atom, bromine atom, or iodine atom.

The term "lower alkyl", as used herein, means straight or branched chain alkyl groups containing 1 to 6 carbon atoms. Examples of lower alkyl include, but are not limited to, methyl, ethyl, propyl, isopropyl, butyl, isobutyl, tert-butyl, sec-butyl, pentyl, neopentyl, hexyl and etc.

The term "protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

The term "amino-protecting group", as used herein, means a protecting group which can be conventionally used to substitute the acidic proton of the amino group. Examples of amino protecting group include, but are not limited to, methyl, ethyl, cyclopropylmethyl, 1-methyl-1-cyclopropylmethyl, diisopropylmethyl, 9-fluorenylmethyl, 9-(2-thio) fluorenylmethyl, 2-furanylmethyl, 2,2,2-trichloromethyl, 2-halomethyl, 2-iodoethyl, 2-trimethylsilylethyl, 2-methylthioethyl, 2-methylsulfonylethyl, 2-(p-toluenesulfonyl) ethyl, 2-phosphonioethyl, 1,1-dimethyl-3-(N,N-dimethylformamido)propyl, 1,1-diphenyl-3-(N,N-diethylamimo) propyl, 1-methyl-1-(adamantanyl)ethyl, 1-methyl-1-phenyethyl, 1-methyl-1-(3,5-dimethoxyphenyl)ethyl, 1-methyl-1-(4-biphenyl)ethyl, 1-methyl-1-(p-phenylazophenyl)ethyl, 1,1-dimethyl-2,2,2-trichloroethyl, 1,1-dimethyl-2-cyanoethyl, isobutyl, t-butyl, t-pentyl, cyclobutyl, 1-methylcyclobutyl, cyclopentyl, cyclohexyl, 1-methylcyclohexyl, 1-adamantly, isobornyl, vinyl, allyl, cinnamyl, phenyl, 2,4,6-tri-t-butylphenyl, m-nitrophenyl, S-phenyl, 8-quinolyl, N'-hydroxypiperidinyl, 4-(1,4-dimethylpiperidinyl), 4,5-diphenyl-3-oxazolin-2-one, benzyl, 2,4,6-trimethylbenzyl, p-methoxybenzyl, p-methoxybenzyloxycarbonyl, 3,5-dimethoxybenzyl, p-decyloxybenzyl, p-nitro-benzyl, p-nitrobenzyloxycarbonyl, o-nitrobenzyl, 3,4-dimethoxy-6-nitrobenzyl, p-bromobenzyl, chlorobenzyl, 2,4-dichlorobenzyl, p-cyanobenzyl, o-(N,N-dimethylformamido)benzyl, m-chloro-p-acyloxybenzyl, p-(dihydroxyboryl)-benzyl, p-(phenylazo)benzyl, p-(p-methoxyphenylazo)benzyl, 5-benzoisoxazolylmethyl, 9-anthrylmethyl, diphenylmethyl, phenyl(o-nitrophenyl)methyl, di(2-pyridyl)methyl, 1-methyl-1-(4-pyridyl)ethyl, isonicotinyl, S-benzyl, N'-piperidinylcarbonyl, carbamate of N'-p-toluenesulfonylaminocarbonyl and N'-phenylaminothiocarbonyl; formyl, acetyl, acetyl-pyridinium, (N'-dithiobenzyloxycarbonylamino)acetyl, 3-phenylpropionyl, 3-(p-hydroxyphenyl)propionyl, 3-(o-nitrophenyl)propionyl, 2-methyl-2-(o-nitrophenoxy)-propionyl, 2-methyl-2-(o-phenylazophenoxy)propionyl, 4-chlorobutyryl, isobutyryl, o-nitrocinnamoyl, pyridylformyl, N'-acetylmethionyl, N'-benzoyl-phenylalkyl, benzoyl, p-phenybenzoyl, p-methoxybenzoyl, o-nitrobenzoyl, amide of o-(benzoyloxymethyl)benzoyl and p-P-benzoyl; the cyclic imides of phthaloyl, 2,3-diphenylmaleoyl and dithiosuccinoyl; t-butoxycarbonyl, allyl, allyloxycarbonyl, phenacyl, 3-acetoxypropyl, 4-nitro-1-cyclohexyl-2-oxo-3-pyrrolidin-3-yl, quaternary ammonium salts, methoxymethyl, 2-chloroethoxymethyl, benzyloxymethyl, pivaloylmethyl, [1-(alkoxycarbonylamino)]-2,2,2,trifluoroethyl, [1-trifluoromethyl-1-(p-chlorophenoxymethoxy)-2,2,2-trifluoro] ethyl, 2-tetrahydro-pyranyl, 2,4-dinitrophenyl, benzyl, 3,4-dimethoxybenzyl, o-nitrobenzyl, di(p-methoxyphenyl) methyl, triphenylmethyl, (p-methoxyphenyl) diphenylmethyl, diphenyl-4-pyridylmethyl, 2-pyridylmethyl-N'-oxide, 5-diphenylpropylsuberyl, N',N'-dimethylaminomethylene, N'-isopropylidene, benzylidene, p-methoxy-benzylidene, p-nitrobenzylidene, salicylidene, 5-chlorosalicylidene, diphenylmethylene, (5-chloro-2-hydroxyphenyl)phenylmethylene, acylvinyl, 5,6-dimethyl-3-oxo-1-cyclohexenyl, borane, [phenyl(pentacarbonylchromium)]carbonyl or [phenyl(pentacarbonyltungsten)] carbonyl, copper or zinc chelate, nitro, nitroso, oxide, diphenylphosphino, dimethylthiophosphinyl, diphenylthiophosphinyl, diethyl phosphoryl, dibenzyl phosphoryl, diphenyl phosphoryl, phosphoryl, trimethylsilyl, benzenesulfanyl, o-nitrobenzenesulfanyl, 2,4-dinitrobenzenesulfanyl, 2-nitro-4-methoxybenzenesulfanyl, triphenylmethylsulfanyl, benzenesulfonyl, p-methoxybenzenesulfonyl, 2,4,6-trimethylbenzenesulfonyl, methylsulfonyl, phenylmesyl, p-toluenemesyl, trifluoromethylsulfonyl, phenacylsulfonyl, diazo etc.

The term "carboxyl protecting group", as used herein, means a protecting group which can be conventionally used to substitute the acidic proton of the carboxylic acid. Examples of carboxyl protecting group include, but are not limited to, methoxymethyl, methylthiomethyl, tetrahydropyran, tetrahydrofuranyl, methoxyethylmethyl, benzyloxymethyl, phenacyl, p-bromophenacyl, α-methylphenacyl, p-methoxyphenacyl, diacylmethyl, N-phthalimidomethyl, ethyl, 2,2,2-trichloroethyl, 2-haloethyl, ω-chloroalkyl, 2-(trimethylsilyl)ethyl, 2-methylthioethyl, 2-(p-nitrothiophenyl) ethyl, 2-(p-methylthiophenyl)ethyl, 1-methyl-1-phenylethyl, t-butyl, cyclopentyl, cyclohexyl, di(o-nitrophenyl)methyl, 9-fluorenylmethyl, 2-(9,10-dioxo)fluorenylmethyl, 5-dithiophenyl, 2,4,6-trimethylbenzyl, p-bromobenzyl, o-nitrobenzyl, p-nitrobenzyl, p-methoxybenzyl, piperonyl, 4-pyridinylmethyl, trimethylsilyl, triethylsilyl, t-butyldimethylsilyl, isopropyldimethylsilyl, phenyldimethylsilyl, S-t-butyl, S-phenyl, S-2-pyridyl, N-hydroxypiperidinyl, N-hydroxysuccinimido, N-hydroxyphthalimido, N-hydroxybenzotriazolyl, O-acyloxime, 2,4-dinitrothiophenyl, 2-alkyl-1,3-oxazoline, 4-alkyl-5-oxo-1,3-oxazolidine, 5-alkyl-4-oxo-1,3-dioxane, triethylstannane, tri-n-butylstannane, N,N'-diisopropylhydrazide, etc.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "salt" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include both organic base addition salts and inorganic base addition salts. Examples of base include, but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

The pharmaceutically acceptable salts of compounds of the present invention are organic acid salts, inorganic acid salts, organic base or inorganic base salts, wherein organic acids include acetic acid, trifluoroacetic acid, methanesulfonic acid, toluenesulfonic acid, maleic acid, succinic acid, tartaric acid, citric acid, and fumaric acid; inorganic acids include hydrochloric acid, hydrobromic acid, nitric acid, sulphuric acid, and phosphoric acid; organic bases include meglumine and dextrosamine; inorganic bases include the alkaline compounds of sodium, potassium, barium, calcium, magnesium, zincium and lithium. It is obvious to those skilled in the art that the pharmaceutically acceptable salts of the compounds of present invention can be formed at the free carboxyls of said compounds by using conventional procedures. The preferred pharmaceutically acceptable salts are sodium salts and potassium salts.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt, ester, and/or prodrug of the present compound may also exist in a solvate form. The solvate is typically formed via hydration which is either part of the preparation of the present compound or through natural absorption of moisture by the anhydrous compound of the present invention.

The term "ester" means any ester of a present compound in which any of the —COOH functions of the molecule is replaced by a —COOR function, in which the R moiety of the ester is any carbon-containing group which fauns a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo. These esters may be conventional ones, including lower alkanoyloxyalkyl esters, e.g. pivaloyloxymethyl and 1-pivaloyloxyethyl esters; lower alkoxycarbonylalkyl esters, e.g., methoxycarbonyloxymethyl, 1-ethoxycarbonyloxyethyl, and 1-isopropylcarbonyloxyethyl esters; lower alkoxymethyl esters, e.g., methoxymethyl esters, lactonyl esters, benzofuran keto esters, thiobenzofuran keto esters; lower alkanoylaminomethyl esters, e.g., acetylaminomethyl esters. Other esters can also be used, such as benzyl esters and cyano methyl esters. Other examples of these esters include: (2,2-dimethyl-1-oxypropyloxy)methyl esters; (1RS)-1-acetoxyethyl esters, 2-[(2-methylpropyloxy)carbonyl]-2-pentenyl esters, 1-[[(1-methylethoxy)carbonyl]-oxy]ethyl esters; isopropyloxycarbonyloxyethyl esters, (5-methyl-2-oxo-1,3-dioxole-4-yl)methyl esters, 1-[[(cyclohexyloxy)carbonyl] oxy]ethyl esters; 3,3-dimethyl-2-oxobutyl esters. It is obvious to those skilled in the art that hydrolysable esters of the compounds of the present invention can be formed at free carboxyls of said compounds by using conventional methods. Preferred esters include pivaloyloxymethyl esters, isopropyloxycarbonyloxyethyl esters and (5-methyl-2-oxo-1,3-dioxole-4-yl)methyl esters.

The term "prodrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug can be an ester or an ether form of a pharmaceutically active compound. Various types of prodrug have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these prodrugs with commonly employed techniques of organic synthesis.

The term "carrier", "vehicle", "diluent", "adjuvant", or "excipient" refers to a substance with which a compound of the present invention is administered.

The term "patient" refers to mammal, preferably human.

The term "treatment" or "treating", as used herein, covers any treatment of a disease and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition, i.e., arresting its development; and (iii) relieving the disease, disorder and/or condition, i.e., causing regression of the disease, disorder and/or condition.

The term "therapeutically effective amount" means the amount of a compound of the present invention, when administered to a patient for treating a disease or other undesirable medical condition, is sufficient to have a beneficial effect with respect to that disease or condition. The therapeutically effective amount will vary depending on the crystalline form, the disease or condition and its severity, and the age, weight, etc. of the patient to be treated. Preferably, a minimal amount is administered, and the amount is escalated in the absence of dose-limiting toxicity to a minimally effective amount. Determination and adjustment of a therapeutically effective amount, as well as evaluation of when and how to make such adjustments, are known to those of ordinary skill in the art.

Therapeutic Use:

In one embodiment, the present invention provides a pharmaceutical composition comprising a compound of the present invention, or a pharmaceutically acceptable salt, solvate, ester, and/or prodrug thereof; and one or more pharmaceutically acceptable carrier. Preferably, the compound in the pharmaceutical composition is in a therapeutically effective amount. Methods known in the art can be applied to formulate any clinically or pharmaceutically acceptable dosage forms, preferably oral or injectable formations, comprising a compound of the present invention in a physiologically effective amount ranging from about 0.01 to about 10 g, e.g., about 0.01 g, about 0.015 g, about 0.02 g, about 0.025 g, about 0.03 g, about 0.04 g, about 0.05 g, about 0.1 g, about 0.125 g, about 0.2 g, about 0.25 g, about 0.3 g, about 0.4 g, about 0.5 g, about 0.6 g, about 0.75 g, about 1 g, about 1.25 g, about 1.5 g, about 1.75 g, about 2 g, about 2.5 g, about 3 g, about 4 g, about 5 g, about 6 g, about 7 g, about 8 g, about 9 g, about 10 g, etc.

The compounds of the of the present invention, or a pharmaceutically acceptable salt, solvate, ester, and/or prodrug thereof, can be administered to a patient through oral or parenteral route in any suitable formulation.

When the compound is administered through parenteral routes, it can be formulated into an injectable dosage form. The term "an injectable dosage form" as used herein, refers to the formulation made of the compound and being injectable, which comprises solutions, emulsions or suspensions, or the sterile powders or concentrated solutions for reconstitution or dilution into sterile injectable solutions or suspensions immediately before use. The injectable dosage form can be classified into an injectable liquid, a sterile powder for injection, and a concentrated solution for injection. The term "injectable liquid" as used herein, refers to a sterile liquid containing the present compound for solution-type injection, emulsion injection or suspension injection made of the compound, which can be administrated via intramuscular injection, intravenous injection, intravenous infusion. The specifications of the volume of the injection may be 1 ml, 2 ml, 5 ml, 10 ml, 20 ml, 50 ml, 100 ml, 200 ml, 250 ml, 500 ml and etc, of which the large volume (usually not less than 100 ml) injection for intravenous infusion is also known as an intravenous feeding. The term "sterile powder for injection" as used herein, refers to the sterile powder or clumpy substance made of the compound for reconstituting into an injectable solution or homogeneous suspension with a suitable sterile solution immediately before use. It can be used as injection after being reconstituted with suitable solvent for injection, as intravenous infusion after being reconstituted with intravenous transfusion. The sterile powder can be prepared by means of crystallization with solvent, spray drying, or lyophilization (i.e. freeze-dried) methods. The term "concentrated solution for injection" as used herein, means the sterile concentrated solution made of the compound, which can be diluted for intravenous infusion just prior to use.

The injectable dosage form can be produced by the conventional methods in the art of formulations, and aqueous solvents or non-aqueous solvents may be selected. The most commonly used aqueous solvent is water for injection, as well as 0.9% sodium chloride solution or other suitable aqueous solutions. The commonly used non-aqueous solvent is vegetable oil, mainly soy bean oil for injection, and others aqueous solutions of alcohol, propylene glycol, polyethylene glycol, and etc. During the preparation of an injectable dosage form, additives may not be used or may be used, and suitable additives may also be added in accordance with the nature of the compounds, such as osmotic pressure regulators, pH regulators, solubilizers, fillers, antioxidants, antibacterial agents or preservatives, emulsifiers, suspending agents, and so on. Commonly used osmotic pressure regulators include sodium chloride, glucose, potassium chloride, magnesium chloride, calcium chloride, sorbitol, etc., preferably sodium chloride or glucose. Commonly used pH regulators include acetic acid-sodium acetate, lactic acid, citric acid-sodium citrate, sodium bicarbonate-sodium carbonate, etc. Commonly used solubilizers include polysorbate 80, propylene glycol, lecithin, polyoxyethylenated castor oil, etc. Commonly used fillers include lactose, mannitol, sorbitol, dextran, etc. Commonly used antioxidants include sodium sulfite, sodium bisulfate, sodium pyrosulfite, etc. Commonly used antibacterial agents or preservatives include phenol, cresol, trichlorobutanol, etc. Commonly used containers for injection include glass ampoules, glass bottles, plastic ampoules, plastic bottles, etc.

When the compound is administered orally, it can be formulated into solid dosage forms for oral administration, for example, tablets, capsules, pills, granules, and so on. It also can be formulated into liquid dosage forms for oral administration, such as oral solutions, oral suspensions, syrups and the like. The term "tablets" as used herein, refers to those solid preparations which are prepared by homogeneously mixing and pressing the compounds and suitable auxiliary materials into circular or irregular troches, mainly in common tablets for oral administration, including also buccal tablets, sublingual tablets, buccal wafer, chewable tablets, dispersible tablets, soluble tablets, effervescent tablets, sustained-release tablets, controlled-release tablets, enteric-coated tablets and the like. The term "capsules" as used herein, refers to those solid preparations which are prepared by filling the compounds, or the compounds together with suitable auxiliary materials into hollow capsules or sealing into soft capsule materials. According to the solubility and release property, capsules can be divided into hard capsules (regular capsules), soft capsules (soft shell capsules), sustained-release capsules, controlled-release capsules, enteric-coated capsules and the like. The term "pills" as used herein, refers to spherical or near-spherical solid preparations which are prepared by mixing the compounds and suitable auxiliary materials via suitable methods, including dropping pills, dragee, pilule and the like. The term "granules" as used herein, refers to dry granular preparations which are prepared by mixing the compounds and suitable auxiliary materials and have a certain particle size. Granules can be divided into soluble granules (generally referred to as granules), suspension granules, effervescent granules, enteric-coated granules, sustained-release granules, controlled-release granules and the like. The term "oral solutions" as used herein, refers to a settled liquid preparation which is prepared by dissolving the compounds in suitable solvents for oral administration. The term "oral suspensions" as used herein, refers to suspensions for oral administration, which are prepared by dispersing the insoluble compounds in liquid vehicles, also including dry suspension or concentrated suspension. The term "syrups" as used herein, refers to a concentrated sucrose aqueous solution containing the compounds.

Suitable carriers for the present invention include, but are not limited to, bulking agents, adhesives, disintegrants, lubricants and the like which can be used for the preparation of the solid dosage forms for oral administration. Commonly used bulking agents include starch, sugar powder, calcium phosphate, calcium sulfate dihydrate, dextrin, microcrystalline cellulose, lactose, pregelatinized starch, mannitol and the like. Commonly used adhesives include sodium carboxymethylcellulose, PVP-K30, hydroxypropyl cellulose, starch slurry, methylcellulose, ethylcellulose, hydroxypropyl methyl cellulose, gelling starch and the like. Commonly used disintegrants include dry starch, crospovidone, croscarmellose, sodium carboxymethyl starch, low-substituted hydroxypropyl cellulose and the like. Commonly used lubricants include magnesium stearate, talc, sodium dodecyl sulfate, micronized silica gel and the like.

It has been found that the carbapenem antibiotics usually are nontoxic to warm blood animals. And this general principle is applicable to the compound of the present invention. When the compounds of present invention are administered to mice in an amount which is higher than the dose for preventing bacteria infections, no distinct poisoning sign or side-effect induced by the compounds of the present invention is observed.

The present invention also provides uses of the present compounds for the treatment of infectious diseases. The compounds of the present invention have excellent antibacterial activities against, gram-positive bacteria, gram-negative bacteria, aerobic bacteria and anaerobic bacteria. The compounds of the present invention have an unexpected super-long half-life, exhibit good stability to β-lactamase and renal dehydropeptidas-I (DHP-I) and can be used to safely treat the diseases caused by a pathogenic microorganism, for example respiratory tract infection and urinary tract infection etc., in mammals (including farm and non-farm animals and pets, such as mouse, rat, rabbit, dog, cat, bull, pig, etc.) including human. In one embodiment, the present invention provides a method of treating an infectious disease in a patient in need thereof. The method comprises administering to the patient a therapeutically effective amount of a compound of the present invention, or a pharmaceutically acceptable salt, solvate, ester, and/or prodrug thereof.

Preparation:

The present compounds can be prepared via methods known to one of ordinary skill in the art. In one embodiment, the present invention provides a process for preparing the present compounds as illustrated in Scheme 1 below:

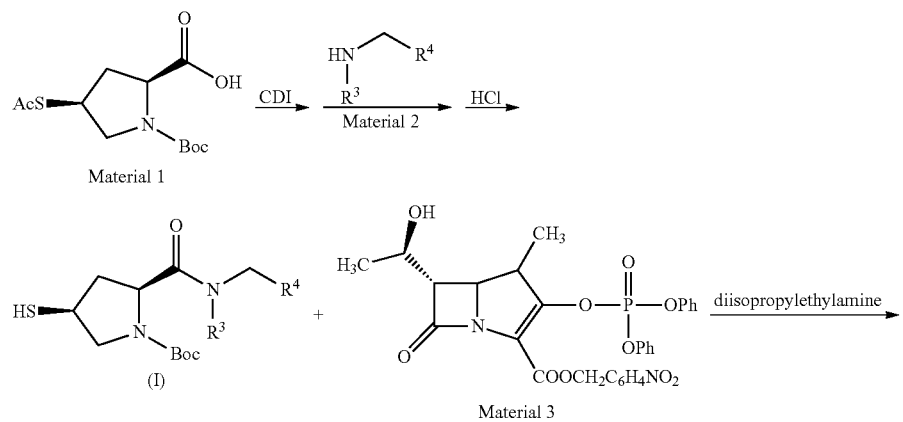

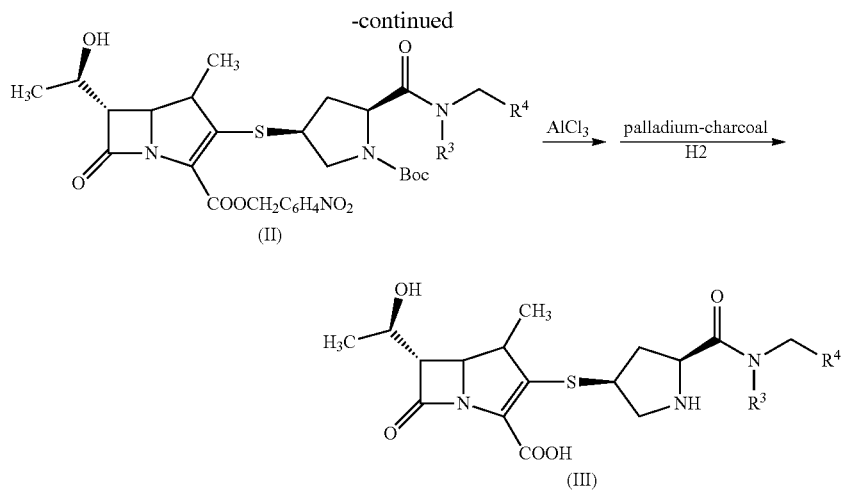

Step 1 Preparation of Intermediate (I):

To an oven dried flask, (2S,4S)-4-(acetylthio)-1-(tert-butoxycarbonyl)pyrrolidine-2-carboxylic acid (Material 1) and anhydrous tetrahydrofuran were added and 1,1-carbonyldiimidazole (CDI) was added thereto at room temperature under a nitrogen atmosphere. A solution of Material 2 in acetone was added to the mixture at 0° C. and the reaction was allowed to continue at that temperature. After the reaction was completed, 1 mol/L of hydrochloride solution was added dropwise; then the mixture was extracted by ethyl acetate. The organic layer was washed successively with water and saturated sodium chloride, and concentrated under reduced pressure. 5 mol/L of hydrochloric acid was then added to the residue. The resultant mixture was stirred and adjusted to basic pH range using a dilute alkaline solution. The resultant precipitates were recrystallized from a mixture of acetonitrile and cyclohexane to give intermediate (I).

Step 2 Preparation of Intermediate (II):

To a flask, a solution of p-nitrobenzyl(4R,5S,6S)-3-(diphenoxyphosphoryloxy)-6-[(1R)-1-hydroxyethyl]-4-methyl-7-oxo-1-aza-bicyclo[3.2.0]hept-2-ene-2-carboxylate (i.e. Material 3) in acetonitrile was added and cooled below −10° C. Then a solution of diisopropylethylamine and intermediate (I) in acetonitrile was added. The reaction mixture was allowed to warm upto 0° C., and the stirring was continued at 0° C. until the reaction was done. After the reaction was completed, ethyl acetate was added to dilute the reaction mixture and the resultant mixture was washed successively with water and saturated brine. The organic layer was then dried and concentrated to give intermediate (II).

Step 3 Preparation of Compound (III):

Intermediate II was dissolved into dichloromethane. Anisole and nitromethane were added into the resultant mixture. The reaction mixture was then cooled to −50° C. A solution of aluminum chloride (1 mol/L) in nitromethane was then added dropwise to the reaction mixture maintained at −50° C. Upon completion of the addition, the reaction mixture was allowed to warm upto −40° C. The reaction mixture was then stirred at −40° C. until the reaction was done. Then water was added; and the precipitate was collected by filtration. The filter cake was then dissolved in a mixture of THF and water, and Pd/charcoal (10%) was added. The reaction mixture was stirred under a hydrogen atmosphere at a pressure of 5 MPa at room temperature. Pd/charcoal was removed by filtration and THF was added to the filtrate. The layers were separated and the aqueous layer was collected. A solution of magnesium chloride in water (5%) was added into the organic (THF) layer. Upon allowing the mixture to stand at room temperature, organic and aqueous layer were separated. The aqueous layer was separated out. The operation was repeated one more time. Aqueous phases were combined and cooled to 0° C.; and methanol was added dropwise while the mixture was maintained at 0° C. The mixture was then cooled to −10° C. and stirred at that temperature, and filtrated. The filter cake was recrystallized to give compound (III); or following the synthetic steps shown here, as a complete or part of procedure, pharmaceutically acceptable salts or esters of the compounds (III) of choice can also be synthesized.

The materials and reagents used in the reactions in the above-mentioned processes can be purchased from a commercial source or synthesized via methods known to one of ordinary skill in the art. For example, Material 1 may be purchased from Shanghai Qiude Biochemical Engineering Co., Ltd; Material 2 may be purchased from AlfaAesara (Tianjin) Chemistry Co., Ltd; Material 3 may be purchased from Xingxiang Hongchen Science and Technology Co., Ltd; and Pd/charcoal may be purchased from Shanghai Hufeng Biotechnology Co., Ltd. Substituents $R^3$ and $R^4$ in the reaction scheme above are as hereinbefore defined; carboxyl group of the compound (III) may be protected by carboxyl protecting groups; hydrogen atom on nitrogen atom can be protected by amino protecting groups as described above.

Assays:

The biological activity of the present compounds were demonstrated by partial in vitro antibacterial tests and pharmacokinetics study in animals. All the compounds of the present invention have the same or similar efficacy as the compounds illustrated in the following examples, which should not be understood in any limiting manner as that the compounds of the present invention only have the following beneficial effect.

Bacterial strains for test: All the bacterial strains are clinically isolated strains obtained from public sources. (1) Gram-positive bacteria: methicillin-sensitive *Staphylococcus aureus* (MSSA), methicillin-resistant *Staphylococcus aureus* (MRSA), methicillin-resistant *Staphylococcus epidermidis* (MRSE), methicillin-sensitive *Staphylococcus epidermidis* (MSSE), penicillin-sensitive *Streptococcus pneumoniae* (PSSP), and penicillin-resistant *Streptococcus pneumoniae* (PRSP); (2) Gram-negative bacteria: *Escherichia coli* (products from ESBLs), *Klebsiella pneumonia*, and *Pseudomonas aeruginosa*.

Drugs to be tested: Compounds 1 to 5, prepared as described above; Control drugs:

Meropenem (Meropenem for injection), Imipenem (Imipenem for injection), commercially available.

Experimental Method: the agar dilution method, by reference to *Methodology of Pharmacological Experiment* (X U Shuyun et al, published by the Peoples Medical Publishing House, 1$^{st}$ Edition, August, 1982; 3$^{rd}$ Edition, 5$^{th}$ printing, January 2002, p 1659-1660).

1 h. 100 ml of hydrochloric acid (1 mol/L) was added dropwise, and the mixture was extracted with ethyl acetate (50 mL×2). The organic layer was washed successively with water and saturated sodium chloride solution, and concentrated under reduced pressure. 200 mL of hydrochloric acid (5 mol/L) was added to the residue and the resultant mixture was stirred for 2 h. The pH of the mixture was adjusted to basic with dilute base solution and precipitate subsequently formed. The precipitated solid was recrystallized to give the titled compound (15.9 g, 86.8%).

TABLE 1

In vitro antibacterial activities of the compounds of the present invention against clinically isolated bacteria

| Bacterial strains | MIC90 (µg/ml) | | | | | | |
|---|---|---|---|---|---|---|---|
| | Imipenem | Meropenem | Compound 1 | Compound 2 | Compound 3 | Compound 4 | Compound 5 |
| (Gram positive) | | | | | | | |
| MSSA | 0.063 | 0.25 | 0.063 | 0.0.125 | 0.063 | 0.031 | 0.063 |
| MRSA | 32 | 64 | 16 | 16 | 32 | 16 | 16 |
| MSSE | 0.031 | 0.125 | 0.031 | 0.063 | 0.031 | 0.031 | 0.063 |
| MRSE | 64 | 64 | 32 | 32 | 32 | 16 | 16 |
| PSSP | 0.016 | 0.031 | 0.016 | 0.016 | 0.031 | 0.016 | 0.016 |
| PRSP | 0.5 | 1 | 0.25 | 0.125 | 0.25 | 0.125 | 0.25 |
| (Gram negative) | | | | | | | |
| *klebsiella pneumonia* | 0.5 | 0.063 | 0.031 | 0.063 | 0.031 | 0.031 | 0.063 |
| *proteus mirabilis* | 8 | 0.25 | 0.125 | 0.125 | 0.25 | 0.125 | 0.125 |
| ESBLs | 0.25 | 0.031 | 0.031 | 0.063 | 0.031 | 0.016 | 0.016 |
| *pseudomonas aeruginosa* | 8 | 4 | 4 | 4 | 2 | 4 | 2 |

Experimental Results and Conclusions: Experimental results are as shown in Table 1. The compounds of the invention exhibit excellent antibacterial activities against the clinically isolates bacteria. The potency of these compounds were better than Imipenem or Meropenem.

Having now generally described the present invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Example 1

Preparation of (2S,4S)-tert-butyl 2-(tert-butoxycarbonyl(4-methoxybenzyl)carbamoyl)-4-mercaptopyrrolidine-1-carboxylate (2S,4S)-4-(acetylthio)-1-(tert-butoxycarbonyl)pyrrolidine-2-carboxylic acid (14.5 g, 50 mmol) and 200 mL of anhydrous tetrahydrofuran were added into a dry flask. 1,1-carbonyldiimidazole (i.e. CDI) (9.8 g, 60 mmol) was added at room temperature under a nitrogen atmosphere. The reaction mixture was stirred for 2 h. The reaction mixture was cooled to below 0° C., a solution of (4-methoxyphenyl)methanamine (7.5 g, 55 mmol) in acetone was added to the reaction mixture below 0° C. and the reaction mixture was stirred for additional Example 2

Preparation of (2S,4S)-tert-butyl 2-(tert-butoxycarbonyl(4-sulfamoylbenzyl)carbamoyl)-4-mercaptopyrrolidine-1-carboxylate The title compound was prepared in a similar manner as described in Example 1, except for replacing (4-methoxyphenyl)methanamine with 10.2 g (55 mmol) of 4-(aminomethyl)benzenesulfonamide. This process afforded Example 2 (16.8 g, 81.1%).

Example 3

Preparation of 3-(3-(((2S,4S)-N,1-bis(tert-butoxycarbonyl)-4-mercaptopyrrolidine-2-carboxamido)methyl)phenyl)propanoic acid The title compound was prepared in a similar manner as described in Example 1, except for replacing (4-methoxyphenyl)methanamine with 9.3 g (52 mmol) of 3-(3-(aminomethyl)phenyl)propanoic acid. This process afforded Example 3 (16.4 g, 80.3%).

Example 4

Preparation of (2S,4S)-tert-butyl 2-(tert-butoxycarbonyl(4-(trifluoromethoxy)benzyl)carbamoyl)-4-mercaptopyrrolidine-1-carboxylate The title compound was prepared in a similar manner as described in Example 1, except for replacing (4-methoxyphenyl)methanamine with 10.5 g (55 mmol) of (4-(trifluoromethoxy)phenyl)methanamine. This process afforded Example 4 (18.8 g, 89.5%).

Example 5

Preparation of (2S,4S)-tert-butyl 2-(tert-butoxycarbonyl(4-(difluoromethoxy)benzyl)carbamoyl)-4-mercaptopyrrolidine-1-carboxylate The title compound was prepared in a similar manner as described in Example 1, except for replacing (4-methoxyphenyl)methanamine with 9.5 g (55 mmol) of (4-(difluoromethoxy)phenyl)methanamine. This process afforded Example 4 (16.9 g, 84.4%).

Example 6

Preparation of (4R,5S,6S)-4-nitrobenzyl 3-((3S,5S)-1-(tert-butoxycarbonyl)-5-(tert-butoxycarbonyl(4-methoxybenzyl)carbamoyl)pyrrolidin-3-ylthio)-6-(R)-1-hydroxyethyl)-4-methyl-7-oxo-1-azabicyclo[3.2.0]hept-2-ene-2-carboxylate A solution of 17.9 g (30 mmol) of p-nitrobenzyl(4R,5S, 6S)-3-(diphenoxy-phosphoryloxy)-6-[(1R)-1-hydroxyethyl]-4-methyl-7-oxo-1-aza-bicyclo[3.2.0]hept-2-ene-2-carboxylate in 150 ml of acetonitrile was added into a flask and the reaction mixture was cooled below −10° C. Then diisopropylethylamine (8 mL) and a solution of Example 1 (10.4 g, 31 mmol) in 100 mL of acetonitrile were added and the reaction mixture was stirred at 0° C. for 15 hours. After the completion of the reaction, ethyl acetate (400 mL) was added to the reaction mixture for dilution and the mixture was washed successively with water and saturated brine. The organic layer was dried and concentrated to give 15.6 g (yield: 73.1%) of Example 6.

Example 7

Preparation of (4R,5S,6S)-4-nitrobenzyl 3-((3S,5S)-1-(tert-butoxycarbonyl)-5-(tert-butoxycarbonyl(4-sulfamoylbenzyl)carbamoyl)pyrrolidin-3-ylthio)-6-(R)-1-hydroxyethyl)-4-methyl-7-oxo-1-azabicyclo[3.2.0]hept-2-ene-2-carboxylate The preparation procedure is similar to that described in Example 6, except for replacing Example 1 with 12.9 g (31 mmol) of Example 2, to give 15.3 g (yield: 66.9%) of Example 7.

Example 8

Preparation of 3-(3-((((2S,4S)-N,1-bis(tert-butoxycarbonyl)-4-((4R,5S,6S)-6-((R)-1-hydroxyethyl)-4-methyl-2-((4-nitrobenzyloxy)carbonyl)-7-oxo-1-azabicyclo[3.2.0]hept-2-en-3-ylthio)pyrrolidine-2-carboxamido)methyl)phenyl)propanoic acid The preparation procedure is similar to that described in Example 6, except for replacing Example 1 with 12.7 g (31 mmol) of Example 3, to give 14.0 g (yield: 62.1%) of Example 8.

Example 9

Preparation of (4R,5S,6S)-4-nitrobenzyl 3-((3S,5S)-1-(tert-butoxycarbonyl)-5-(tert-butoxycarbonyl(4-(trifluoromethoxy)benzyl)carbamoyl)pyrrolidin-3-ylthio)-6-((R)-1-hydroxyethyl)-4-methyl-7-oxo-1-azabicyclo[3.2.0]hept-2-ene-2-carboxylate The preparation procedure is similar to that described in Example 6, except for replacing Example 1 with 13.0 g (31 mmol) of Example 4, to give 16.4 g (yield: 68.7%) of Example 9.

Example 10

Preparation of (4R,5S,6S)-4-nitrobenzyl 3-((3S,5S)-1-(tert-butoxycarbonyl)-5-(tert-butoxycarbonyl(4-(difluoromethoxy)benzyl)carbamoyl)pyrrolidin-3-ylthio)-6-((R)-1-hydroxyethyl)-4-methyl-7-oxo-1-azabicyclo[3.2.0]hept-2-ene-2-carboxylate The preparation procedure is similar to that described in Example 6, except for replacing Example 1 with 12.5 g (31 mmol) of Example 5, to give 15.4 g (yield: 68.7%) of Example 10.

Example 11

Preparation of (4R,5S,6S)-6-((R)-1-hydroxyethyl)-3-((3S,5S)-5-(4-methoxybenzylcarbamoyl)pyrrolidin-3-ylthio)-4-methyl-7-oxo-1-azabicyclo[3.2.0]hept-2-ene-2-carboxylic acid (Compound 1)

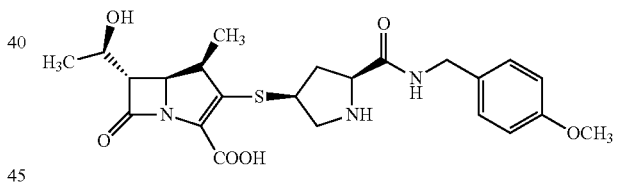

14.2 g (20 mmol) of Example 6 was dissolved in dichloromethane (100 mL). 20 mL of anisole and 30 mL of nitromethane were added therein. The reaction mixture was cooled to −50° C. Then 150 mL of 1 mol/L of aluminum trichloride in nitrometane was added dropwise at −50° C. and stirred for 2 h at −40° C. Water (200 mL) was added to the reaction mixture. The precipitate was collected by filtration. The filter cake was dissolved in a mixed solution of THF (400 mL) and water (30 mL). Palladium/charcoal (5 g, 10%) was then added. The resultant mixture was stirred for 2 h at room temperature and under a hydrogen pressure of 5 MPa. The palladium/charcoal was then removed by filtration. The filtrate was diluted with THF (150 mL), and then partitioned between water and THF. The aqueous layer was collected. 20 mL of 5% aqueous solution of magnesium chloride was added into the THF layer to stand to separate out the aqueous layer, and the operation was repeated one more time. Aqueous phases were combined; and methanol was slowly added dropwise at 0° C. The mixture was then stirred at −10° C. for 1 h, and filtrated. The filter cake was recrystallized to give 4.7 g (yield: 53.4%) of Compound 1, as a white solid.

Molecular formula: $C_{23}H_{29}N_3O_6S$
Molecular weight: 475.56
Elemental analysis:
Found: C, 57.85%; H, 6.34%; N, 8.67%; S, 6.92%.
Calcd.: C, 58.09%; H, 6.15%; N, 8.84%; S, 6.74%.
MS: 476.2 (M+1)
$^1$H-NMR (600 MHz, DMSO) δ: 1.13 (d, 3H), 1.15 (d, 3H), 1.51 (dt, 1H), 2.51-2.60 (m, 2H), 3.16 (d, 1H), 3.28-3.33 (m, 2H), 3.49 (t, 1H), 3.66 (t, 1H), 3.72 (s, 3H), 3.93 (d, 1H), 4.10 (d, 1H), 4.20 (d, 2H), 5.02 (s, 1H), 6.87 (d, 2H), 7.17 (d, 2H), 8.35 (t, 1H).

Example 12

Preparation of (4R,5S,6S)-6-(R)-1-hydroxyethyl)-4-methyl-7-oxo-3-((3S,5S)-5-(4-sulfamoylbenzylcarbamoyl)pyrrolidin-3-ylthio)-1-azabicyclo[3.2.0]hept-2-ene-2-carboxylic acid (Compound 2)

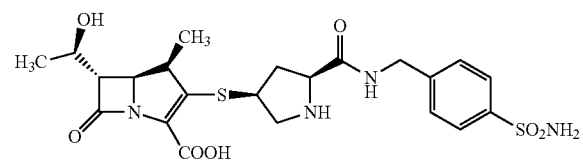

The preparation procedure is similar to that described in Example 11, except for replacing Example 6 with 14.4 g (20 mmol) of Example 7, to give 4.8 g (yield: 50.4%) of Compound 2, as a white solid.
Molecular formula: $C_{22}H_{28}N_4O_7S_2$
Molecular weight: 524.61
Elemental analysis:
Found: C, 50.15%; H, 5.62%; N, 10.45%; S, 12.08%.
Calcd.: C, 50.37%; H, 5.38%; N, 10.68%; S, 12.22%.
MS: 547.2 (M+Na$^+$)
$^1$H-NMR (600 MHz, DMSO) δ: 1.14 (d, 3H), 1.15 (d, 3H), 1.56 (dt, 1H), 2.55 (dt, 1H), 2.62 (dd, 1H), 3.19 (m, 1H), 3.31-3.43 (m, 2H), 3.56 (m, 1H), 3.76 (t, 1H), 3.95 (m, 1H), 4.14 (dd, 1H), 4.33 (m, 2H), 5.02 (br.s, 1H), 7.30 (s, 2H), 7.42 (d, 2H), 7.76 (d, 2H), 8.63 (t, 1H).

Example 13

Preparation of (4R,5S,6S)-3-((3S,5S)-5-(3-(2-carboxyethyl)benzylcarbamoyl)pyrrolidin-3-ylthio)-6-(R)-1-hydroxyethyl)-4-methyl-7-oxo-1-azabicyclo[3.2.0]hept-2-ene-2-carboxylic acid (Compound 3)

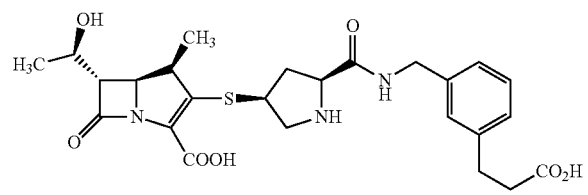

The preparation procedure is similar to that described in Example 11, except for replacing Example 6 with 14.4 g (20 mmol) of Example 8, to give 4.8 g (yield: 50.4%) of Compound 3, as a white solid.

Molecular formula: $C_{25}H_{31}N_3O_7S$
Molecular weight: 517.59
Elemental analysis:
Found: C, 57.83%; H, 6.34%; N, 8.02%; S, 6.24%.
Calcd.: C, 58.01%; H, 6.04%; N, 8.12%; S, 6.20%.
MS: 518.6 (M+1)

Example 14

Preparation of (4R,5S,6S)-6-((R)-1-hydroxyethyl)-4-methyl-7-oxo-3-((3S,5S)-5-(4-(trifluoromethoxy)benzylcarbamoyl)pyrrolidin-3-ylthio)-1-azabicyclo[3.2.0]hept-2-ene-2-carboxylic acid (Compound 4)

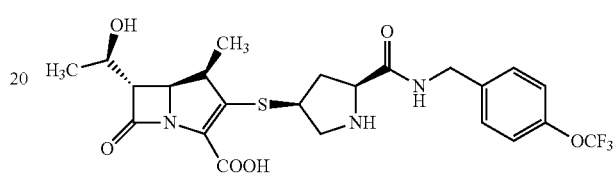

The preparation procedure is similar to that described in Example 11, except for replacing Example 6 with 14.4 g (20 mmol) of Example 9, to give 4.8 g (yield: 50.4%) of Compound 4, as a white solid.
Molecular formula: $C_{23}H_{26}F_3N_3O_6S$
Molecular weight: 529.53
Elemental analysis:
Found: C, 52.01%; H, 5.23%; F, 10.47; N, 7.73%; S, 5.93%.
Calcd.: C, 52.17%; H, 4.95%; F, 10.76; N, 7.94%; S, 6.06%.
MS: 530.5 (M+1)

Example 15

Preparation of (4R,5S,6S)-3-((3S,5S)-5-(4-(difluoromethoxy)benzylcarbamoyl)pyrrolidin-3-ylthio)-6-(R)-1-hydroxyethyl)-4-methyl-7-oxo-1-azabicyclo[3.2.0]hept-2-ene-2-carboxylic acid (Compound 5)

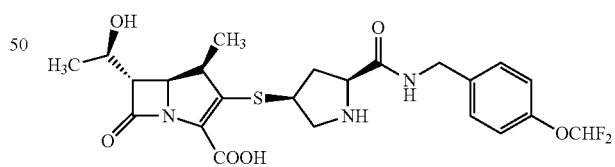

The preparation procedure is similar to that described in Example 11, except for replacing Example 6 with 14.4 g (20 mmol) of Example 10, to give 4.8 g (yield: 50.4%) of Compound 5, as a white solid.
Molecular formula: $C_{23}H_{27}F_2N_3O_6S$
Molecular weight: 511.54
Elemental analysis:
Found: C, 53.87%; H, 5.56%; F, 7.22; N, 8.05%; S, 6.51%.
Calcd.: C, 54.00%; H, 5.32%; F, 7.43; N, 8.21%; S, 6.27%.
MS: 512.54 (M+1)

Example 16

Preparation of Sterile Powders for Injection

1. Formula

| Formula 1: | |
|---|---|
| Compound 1 | 500 g |
| arginine | 500 g |
| Units prepared | 1000 bottles |
| Formula 2: | |
| Compound 2 | 1000 g |
| arginine | 500 g |
| Units prepared | 1000 bottles |
| Formula 3: | |
| Compound 3 | 2000 g |
| arginine | 500 g |
| Units prepared | 1000 bottles |
| Formula 4: | |
| Compound 4 | 1000 g |
| arginine | 250 g |
| Units prepared | 1000 bottles |
| Formula 5: | |
| Compound 5 | 1000 g |
| arginine | 250 g |
| Units prepared | 1000 bottles |

2. Procedure:

The antibiotic glass bottles and rubber plugs used for the preparation were sterilized. In accordance with the formulae above-mentioned, the compounds (being added after conversion) and auxiliary materials (if any) were weighted and subpackaged in a racking machine with measuring the amounts of the loads at any moment. Plugs were inserted in the bottlenecks; covers were pressed. The finished products were entirely inspected, packaged and warehoused.

Example 17

Preparation of Tablets

1. Formula

| Formula 1: | |
|---|---|
| Compound 1 | 250 g |
| Pre-gelatinized starch | 50 g |
| Low-substituted hydroxypropyl cellulose | 40 g |
| Microcrystalline cellulose | 40 g |
| 2% HPMC water solutio | Suitable amounts |
| Micronized silica gel | 4 g |
| Magnesium stearate | 4 g |
| Starch sodium glycolate | 2 g |
| Total units prepared | 1000 tablets |
| Formula 2: | |
| Compound 2 | 250 g |
| Pre-gelatinized starch | 50 g |
| Low-substituted hydroxypropyl cellulose | 40 g |
| Microcrystalline cellulose | 40 g |
| 2% HPMC water solutio | Suitable amounts |
| Micronized silica gel | 4 g |
| Magnesium stearate | 4 g |
| Starch sodium glycolate | 2 g |
| Total units prepared | 1000 tablets |

2. Procedure:

The compounds and excipients were weighted separately according to the proportions in Formulae 1 and 2 above. Dissolve low-substituted hydroxypropyl cellulose in water to make 2% aqueous solution. The compounds were milled and sieved (100 mesh), and the excipients were respectively sieved (100 mesh). The compounds, pre-gelatinized starch (or starch), microcrystalline cellulose, and low-substituted hydroxypropyl cellulose were homogeneously mixed, and a suitable amount of HPMC aqueous solution was then added, and mixed homogeneously with a stir to form suitable soft materials, which were passed through sieves (20 mesh). The resulting granules were dried at 60° C. The dried granules were then mixed with magnesium stearate and micronized silica gel, and then passed through sieves (18 mesh) and were homogeneously mixed. Sampling was performed to inspect the semifinished products. Tabletting was performed according to the tablet weight determined on the basis of the inspection. The finished products were entirely inspected, packaged and warehoused.

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A compound of formula (I):

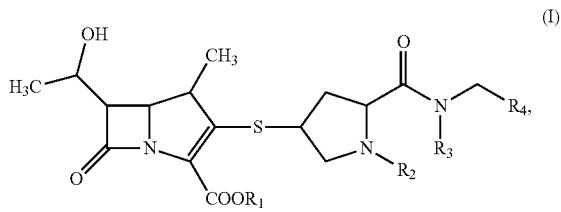

or a pharmaceutically acceptable salt, ester, and/or prodrug thereof;

wherein $R^1$ is hydrogen or a carboxyl protecting group;
$R^2$ is hydrogen or an amino-protecting group;
$R^3$ is hydrogen or lower alkyl; and
$R^4$ is phenyl or substituted phenyl;

wherein the substituted phenyl comprises one or more substituents selected from the group consisting of halogen; hydroxyl; carboxyl; amino; nitro; cyano; lower alkyl; substituted lower alkyl; lower alkoxy; substituted lower alkoxy; aminosulfonyl; lower alkylaminosulfonyl; and a combination thereof;

wherein the substituted lower alkyl and the substituted lower alkoxy each independently comprise one or more substituents selected from the group consisting of halogen; hydroxyl; carboxyl; amino; nitro; cyano; and a combination thereof.

2. A compound of formula (I):

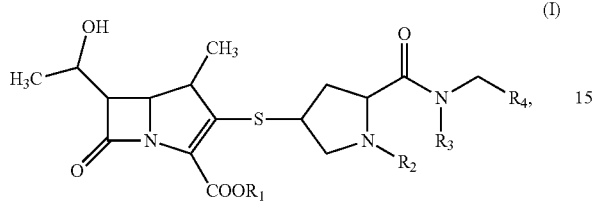

(I)

or a pharmaceutically acceptable salt, ester, and/or prodrug thereof;
wherein
$R^1$ is a hydrogen atom or a carboxyl protecting group;
$R^2$ is a hydrogen atom or an amino-protecting group;
$R^3$ is a hydrogen atom or a lower alkyl; and
$R^4$ is a phenyl or substituted phenyl;
wherein the substituted phenyl comprises one or more substituents selected from the group consisting of sulfo; carbamoyl; lower alkyl; substituted lower alkyl; lower alkoxy; substituted lower alkoxy; lower alkylcarbonyl; substituted lower alkylcarbonyl; lower alkylcarbonyloxy; substituted lower alkylcarbonyloxy; lower alkylsulphonyl; substituted lower alkylsulphonyl; lower alkylamido; substituted lower alkylamido; lower alkylcarbamoyl; substituted lower alkylcarbamoyl; lower alkylsulphonamido; substituted lower alkylsulphonamido; and a combination thereof;

wherein the substituted lower alkyl and the substituted lower alkoxy each independently comprise one or more substituents selected from the group consisting of sulfo; aminosulphonyl; carbamoyl; and a combination thereof;

wherein the substituted lower alkylcarbonyl; the substituted lower alkylcarbonyloxy; the substituted lower alkylsulphonyl; the substituted lower alkylamido; the substituted lower alkylcarbamoyl; and the substituted lower alkylsulphonamido each independently comprise one or more substituents selected from the group consisting of halogen; hydroxyl; carboxyl; amino; nitro; cyano; sulfo; aminosulfonyl; carbamoyl; and a combination thereof.

3. A compound of formula (II):

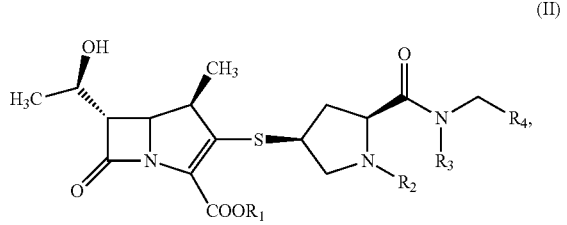

(II)

or a pharmaceutically acceptable salt, ester, and/or prodrug thereof;
wherein
$R^1$ is a hydrogen atom or a carboxyl protecting group;
$R^2$ is a hydrogen atom or an amino-protecting group;
$R^3$ is a hydrogen atom or a lower alkyl; and
$R^4$ is a phenyl or substituted phenyl;

wherein the substituted phenyl comprises one or more substituents selected from the group consisting of sulfo; carbamoyl; lower alkyl; substituted lower alkyl; lower alkoxy; substituted lower alkoxy; lower alkylcarbonyl; substituted lower alkylcarbonyl; lower alkylcarbonyloxy; substituted lower alkylcarbonyloxy; lower alkylsulphonyl; substituted lower alkylsulphonyl; lower alkylamido; substituted lower alkylamido; lower alkylcarbamoyl; substituted lower alkylcarbamoyl; lower alkylsulphonamido; substituted lower alkylsulphonamido; and a combination thereof;

wherein the substituted lower alkyl and the substituted lower alkoxy each independently comprise one or more substituents selected from the group consisting of sulfo; aminosulphonyl; carbamoyl; and a combination thereof;

wherein the substituted lower alkylcarbonyl; the substituted lower alkylcarbonyloxy; the substituted lower alkylsulphonyl; the substituted lower alkylamido; the substituted lower alkylcarbamoyl; and the substituted lower alkylsulphonamido each independently comprise one or more substituents selected from the group consisting of halogen; hydroxyl; carboxyl; amino; nitro; cyano; sulfo; aminosulfonyl; carbamoyl; and a combination thereof.

4. The compound of any of claims 1 to 3, wherein
$R^3$ is hydrogen, methyl, ethyl, or propyl;
$R^4$ is a phenyl or substituted phenyl;
wherein the substituted phenyl comprises one or more substituents selected from the group consisting of halogen; hydroxyl; carboxyl; amino; lower alkyl; substituted lower alkyl; lower alkoxy; substituted lower alkoxy; aminosulfonyl; and a combination thereof;
wherein the substituted lower alkyl and the substituted lower alkoxy each independently comprise one or more substituents selected from the group consisting of halogen; hydroxyl; carboxyl; amino; and a combination thereof.

5. The compound of any of claims 1 to 3, wherein
$R^1$ represents hydrogen atom;
$R^2$ represents hydrogen atom;
$R^3$ represents hydrogen atom or methyl;
$R^4$ is a phenyl or substituted phenyl;
wherein the substituted phenyl comprises one or more substituents selected from the group consisting of methyl; ethyl; carboxyl; carboxymethyl; carboxyethyl; methoxy; trifluoromethoxy; aminosulfonyl; and a combination thereof.

6. The compound of any of claims 1 to 3, which is selected from the group consisting of

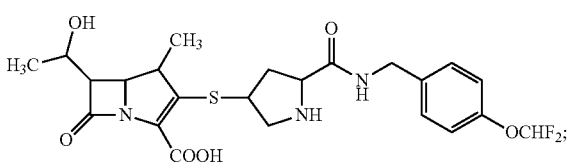

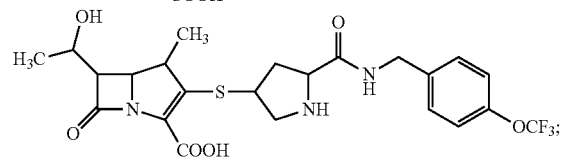

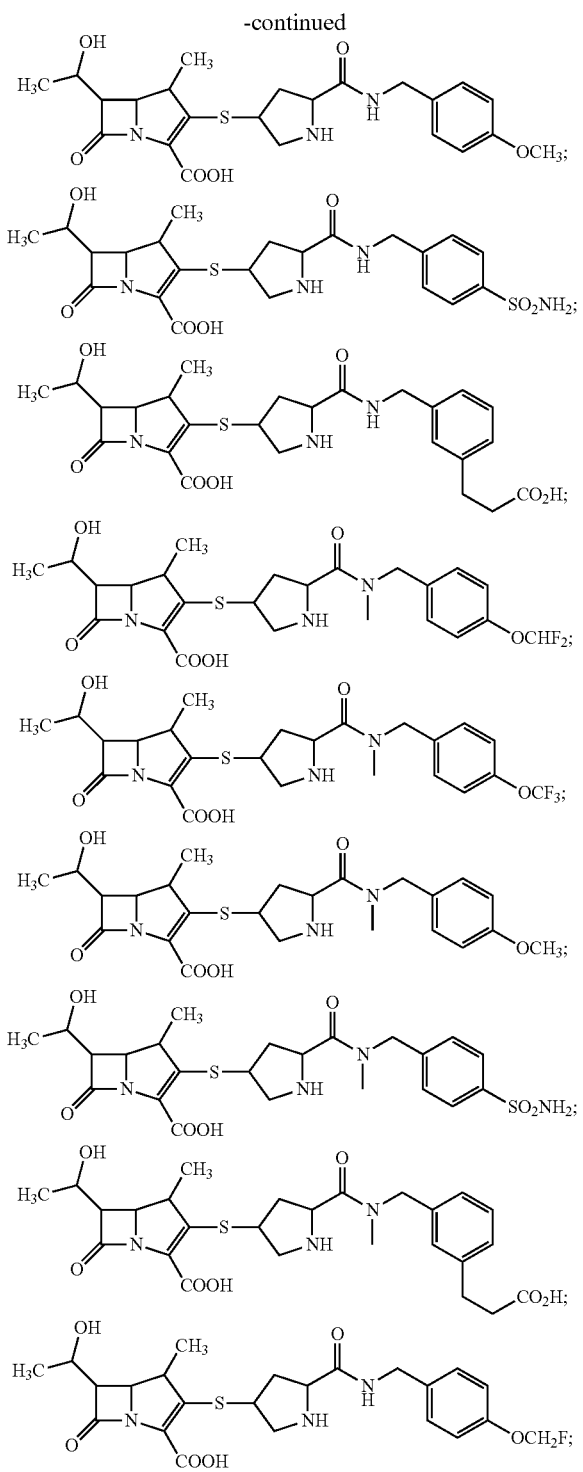

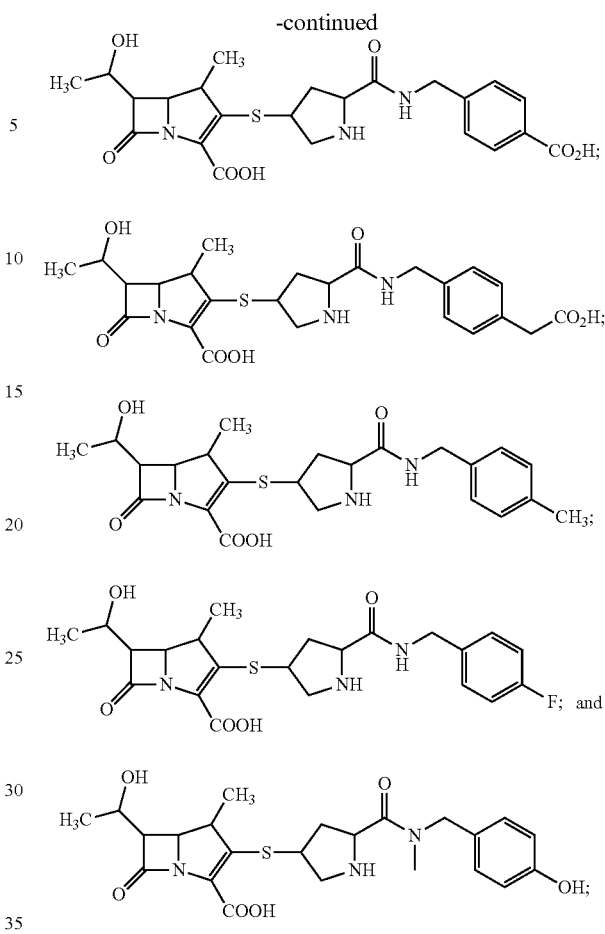

or a pharmaceutically acceptable salt, ester, and/or prodrug thereof.

7. The compound of any of claims 1 to 3, wherein the pharmaceutically acceptable salt is an amino acid salt, or an inorganic base salt.

8. The compound of any of claims 1 to 3, wherein the pharmaceutically acceptable ester is hydrolyzable to the corresponding carboxylic acid in vivo.

9. A pharmaceutical composition comprising a compound of any of claims 1 to 3, or a pharmaceutically acceptable salt, ester, and/or prodrug thereof; and one or more pharmaceutically acceptable carriers.

10. A method of treating a bacterial infection in a patient in need thereof comprising administering to the patient a therapeutically effective amount of a compound of any of claims 1 to 3, or a pharmaceutically acceptable salt, ester, and/or prodrug thereof.

* * * * *